United States Patent
McGrath et al.

(10) Patent No.: US 10,915,590 B2
(45) Date of Patent: *Feb. 9, 2021

(54) CONTROLLING ACCESS TO PROTECTED INFORMATION

(71) Applicant: International Business Machines Corporation, Armonk, NY (US)

(72) Inventors: Damian McGrath, Meath (IE); Meng Qi, Dublin (IE); Bruno Bruzzano, Dublin (IE); Francesco Mariani, Dublin (IE)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/393,147

(22) Filed: Apr. 24, 2019

(65) Prior Publication Data

US 2019/0251134 A1   Aug. 15, 2019

Related U.S. Application Data

(63) Continuation of application No. 15/593,372, filed on May 12, 2017.

(51) Int. Cl.
*G06F 16/00* (2019.01)
*G06F 16/9535* (2019.01)
(Continued)

(52) U.S. Cl.
CPC ...... *G06F 16/9535* (2019.01); *G06F 16/2282* (2019.01); *G06F 21/6245* (2013.01); *G16H 10/60* (2018.01)

(58) Field of Classification Search
None
See application file for complete search history.

(56) References Cited

U.S. PATENT DOCUMENTS

| 7,243,097 B1 | 7/2007 | Agrawal |
| 7,958,150 B2 | 6/2011 | Bird |

(Continued)

FOREIGN PATENT DOCUMENTS

KR   101120814 B1   8/2005

OTHER PUBLICATIONS

"Scenario: ExampleBANK using row and column access control—Database users and roles", IBM Knowledge Center, Printed on Apr. 18, 2017, <http://www.ibm.com/support/knowledgecenter/SSEPGG_10.1.0/com.ibm.db2.luw.admin.sec.doc/doc/c0058832.html>, 3 pages.

(Continued)

*Primary Examiner* — Anhtai V Tran
(74) *Attorney, Agent, or Firm* — Stephen R. Yoder; David B. Woycechowsky

(57) ABSTRACT

Controlling access to protected information stored in a database. Certain records in the database can be designated as master records. Master records are stored in a data table. Any database record of the database may include one or more ownership data fields comprising owner identification information for identifying a master record associated with the database record. Owner identification information of the ownership data fields of a retrieved database record are analyzed to identify the master record associated with the retrieved database record. Access to the retrieved database record is controlled using the same authorization rules used to govern access to the master record associated with the retrieved database record. The system provides a mechanism to ensure that the owner identification information of any new or updated database record is linked to the correct master records. New and updated database records inherit access control from their associated master records.

3 Claims, 6 Drawing Sheets

(51) Int. Cl.
*G06F 21/62* (2013.01)
*G16H 10/60* (2018.01)
*G06F 16/22* (2019.01)

(56) References Cited

U.S. PATENT DOCUMENTS

| | | | |
|---|---|---|---|
| 8,478,713 B2 | 7/2013 | Cotner | |
| 8,775,470 B2 | 7/2014 | Bird | |
| 8,983,985 B2 | 3/2015 | Chen | |
| 9,323,947 B1 | 4/2016 | Harding | |
| 9,355,273 B2 | 5/2016 | Stevens | |
| 9,619,552 B2 | 4/2017 | Falter | |
| 2005/0004895 A1 | 1/2005 | Schurenberg | |
| 2005/0236474 A1 | 10/2005 | Onuma | |
| 2009/0182747 A1 | 7/2009 | Bird | |
| 2015/0019254 A1 | 1/2015 | Ibikunle | |
| 2015/0281248 A1* | 10/2015 | Obbard | G06F 16/23 726/1 |
| 2016/0283663 A1 | 9/2016 | Allen | |
| 2016/0292453 A1 | 10/2016 | Patterson | |
| 2016/0342812 A1 | 11/2016 | Lynch | |
| 2017/0372012 A1* | 12/2017 | Motoki | G16H 10/60 |
| 2018/0150650 A1* | 5/2018 | Saunders | G06F 19/00 |
| 2018/0330113 A1 | 11/2018 | Mcgrath | |
| 2018/0330114 A1 | 11/2018 | Mcgrath | |

OTHER PUBLICATIONS

Agrawal et al., "Extending Relational Database Systems to Automatically Enforce Privacy Policies", Provided by inventor in Post Disclosure Comments dated Oct. 26, 2016, 10 pages, <www.almaden.ibm.com/cs/projects/iis/hdb/Publications/papers/fgac_icde05.pdf>.

Andal et al., "Ensuring Access Control in Cloud Provisioned Healthcare Systems", provided in Search Report dated Nov. 23, 2016, <https://www.cse.unr.edu/~mgunes/papers/eHealth11.pdf>, 5 pages.

Rjaibi, Walid, "A practical guide to implementing row and column access control" DB2 for Linux, UNIX, and Windows Best Practices Wiki, Apr. 16, 2013, 4 pages.

Sehta et al., "A Fine Grained Access Control Model for Relational Databases", (IJCSIT) International Journal of Computer Science and Information Technologies, vol. 3 (1), 2021, 3183-3186.

Steele et al., "HealthPass: Fine-grained Access Control to Portable Personal Health Records", 2010 24th IEEE International Conference on Advanced Information Networking and Applications, pp. 1012-1019.

List of IBM Patents or Patent Applications Treated as Related, Filed Apr. 24, 2019, 2 pages.

* cited by examiner

CONTROLLING ACCESS TO PROTECTED INFORMATION

BACKGROUND

The present invention relates to the field of controlling access to protected information stored in a database such as confidential information, sensitive data, Protected/Personal Health Information (PHI), etc.

The present invention further relates to a computer program product comprising computer-readable program code that enables a processor of a system to implement such a method.

The present invention yet further relates to a system for controlling access to protected information stored in a database such as confidential information, sensitive data, PHI, etc.

The use of computers to store confidential information, such as patient medical data records, is well known. Conventional security measures, such as user passwords, are typically used to prevent unauthorized access to the patient medical records.

In one example, the Health Insurance Portability and Accountability Act of 1966, known as HIPAA, mandates security for protected health information by organizations, such as hospitals. However, in some circumstances, it may be desirable to limit access to patient data records independent of any regulatory requirement.

SUMMARY

Some embodiments of the present invention seek to provide a method for controlling access to protected information stored in a database.

Some embodiments of the present invention further seek to provide a computer program product including computer program code for implementing the method when executed on a processor of a data processing system.

Some embodiments of the present invention yet further seek to provide a data storage system adapted to execute this computer program code.

Some embodiments of the present invention also seek to provide a system for controlling access to protected information stored in a database.

According to an embodiment of the present invention there is provided a computer-implemented method for controlling access to protected information stored in a database. A set of database records in various data tables may be identified as being master records. In each database record of the database, there may be stored one or more ownership data fields comprising owner identification information for identifying a master record associated with the database record. A database record of the database may be retrieved and the owner identification information of the ownership data fields of the retrieved database record may be analyzed to identify the master record associated with the retrieved database record. Access to the retrieved database record may then be controlled using the same one or more authorization rules used to govern access to the master record associated with the retrieved database record.

According to another embodiment of the present invention, there is provided a computer program product for controlling access to protected information stored in a database. The computer program product comprises a computer readable storage medium having program instructions embodied therewith, the program instructions executable by a processing unit to cause the processing unit to perform a method according to an embodiment of the invention.

According to another embodiment of the invention, there is provided a data storage system comprising at least one processor and the computer program product according to an embodiment. The at least one processor is adapted to execute the computer program code of said computer program product.

According to yet another embodiment of the invention, there is provided a system for controlling access to protected information stored in a database. The system comprises: an ownership storage unit adapted to store a plurality of ownership rules in a data table, each ownership rule designating database records of a data table as master records. The system also comprises a database storage unit adapted to store, in each database record of the database, one or more ownership data fields comprising owner identification information for identifying a master record associated with the database record. The system also comprises a data retrieval unit adapted to retrieve a database record of the database. The system also comprises an authorization control unit adapted to analyze the owner identification information of the ownership data fields of the retrieved database record to identify the master record associated with the retrieved database record and to control access to the retrieved database record using the same on or more authorization rules governing access to the master record.

BRIEF DESCRIPTION OF THE DRAWINGS

Preferred embodiments of the present invention will now be described, by way of example only, with reference to the following drawings, in which.

DETAILED DESCRIPTION

Figure 1:
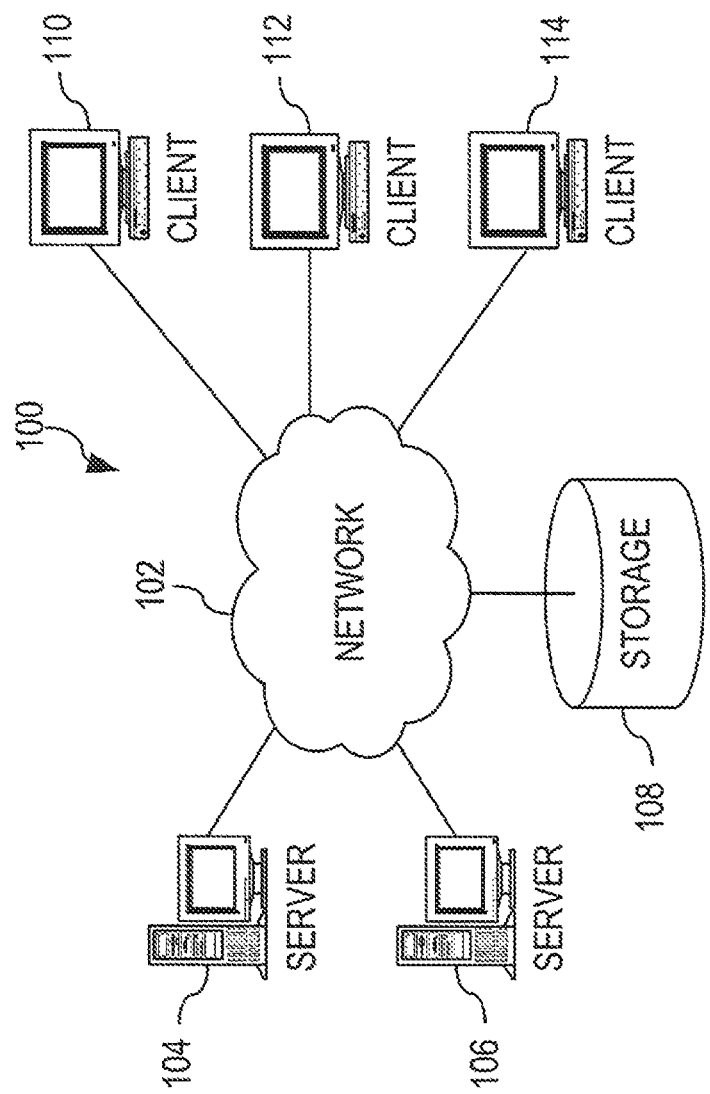
FIG. 1 depicts a pictorial representation of an example distributed system in which aspects of the illustrative embodiments may be implemented.

It should be understood that the Figures are merely schematic and are not drawn to scale. It should also be understood that the same reference numerals are used throughout the Figures to indicate the same or similar parts.

In the context of the present application, where embodiments of the present invention constitute a method, it should be understood that such a method is a process for execution by a computer, i.e. is a computer-implementable method. The various steps of the method therefore reflect various parts of a computer program, e.g. various parts of one or more algorithms.

Also, in the context of the present application, a system may be a single device or a collection of distributed devices that are adapted to execute one or more embodiments of the methods of the present invention. For instance, a system may be a personal computer (PC), a server or a collection of PCs and/or servers connected via a network such as a local area network, the Internet and so on to cooperatively execute at least one embodiment of the methods of the present invention.

Proposed is a concept for controlling access to protected information stored in a database (such as PHI for example). By employing a mechanism to identify master records, the permission(s) associated with a master record may be inherited by database records that identify that master record as being their associated 'owner'. For example, by designating some records in some rows of a data table as master records, permissions associated with a row may be linked to all database records that designate that row as being its owner. In this way, effective execution of Ownership-Oriented Row-Based Authorization (OORBA) decisions is therefore based on an ability to efficiently retrieve the permissions of a Master Row associated with any given row to which OORBA applies.

Thus, an approach to controlling access to protected information stored in a database may be provided. Certain records in the database may be designated as master records, and the master records stored may be stored in a data table. A database record of the database may then include one or more ownership data fields comprising owner identification information for identifying a master record associated with the database record. Owner identification information of the ownership data fields of a retrieved database record may then be analyzed to identify the master record associated with the retrieved database record. Access to the retrieved database record may then be controlled using the same one or more authorization rules used to govern access to the master record associated with the retrieved database record.

Also, such a proposed approach may provide a mechanism to ensure that the owner identification information of any new or updated database record is linked to the correct master records. For example, embodiments may further comprise the step of associating a newly created or updated database record in the data with a master record. Such a step of associating may comprise: processing the newly created or updated database record by analyzing an ownership meta-data table to determine which master record the database record should be associated with. In this way, new and updated database records may inherit access control from their associated master records.

In each database record of the database, one or more ownership data fields may be provided and may comprise owner identification information (such as metadata) for identifying a master record associated with the database record. Thus, such owner identification information of the ownership data fields of a retrieved database record may be analyzed to identify the master record associated with the retrieved database record. Authorization of access to the retrieved database record may then be performed using the same authorization rule(s) as those used to control access to its associated master record.

In some embodiments of the system, extensions to the Data Definition Language (DDL) are used to allow a database designer to define data ownership rules. Extensions to the DDL language processor in this embodiment may then allow data ownership rules to be stored in an ownership meta-data table for a database. In these embodiments, each of the master records is identified by the DataBase Management System which processes the ownership meta-data. Embodiments may therefore build on existing row-based authorization for relational databases by adding a capability to automatically attribute row-based permissions to newly added or updated data rows such that only users who are permitted to access a database record may do so. Such an approach may overcome shortcomings of existing row-based authorization schemes. For example, the problem of ensuring that code always adds correct permissions every time data is inserted or updated, or the problem of ensuring that multiple applications are permitted access to the same data in a consistent manner.

Also, by way of example, the ownership data fields may comprise: a flag field comprising information for indicating whether the database record has an associated master record; and an owner identification field comprising information identifying a master record associated with the database record. For instance, the owner identification field may comprise a key (e.g., a 64-bit integer) of the master record associated with the database record. The ownership data fields may also include a table identification field comprising information identifying a data table comprising the master record associated with the database record. In this way, the ownership data fields may identify a storage location of the master record within a plurality of data tables. Embodiments may therefore implement multiple data tables.

Accordingly, there may be provided an approach to extend relational database management systems such that newly added or updated rows in tables containing protected information are automatically attributed with the correct row-based permissions in the same transaction in which the data is inserted or updated.

Embodiments may also provide concepts for the storage of data records that facilitate the efficient authorization and auditing of all attempted access to a protected data.

By way of further example, some embodiments include extensions to a Data Definition Language (DDL) for indicating how permissions can propagate to new data rows. Such extensions may provide constraints on how a database schema should preferably be designed in order to take advantage of the DDL extensions. In this way, a developer may assist in the provision of appropriate code.

Also, it is noted that, although embodiments are presented in the context of being applicable in the relation to healthcare and/or PHI, applicability of the proposed concepts may extend to other fields where access to data may need to be controlled/regulated and/or where relational databases are in use. For example, embodiments may be implemented in relation to a relational database for a multi-tenanted application where users from one tenant must never be permitted to access data belonging to another tenant.

Illustrative embodiments may therefore provide concepts for controlling access to protected data records in a relational database. Dynamic OORBA and access control concepts may therefore be provided by proposed embodiments.

Modifications and additional steps to a traditional data storage and retrieval systems may also be proposed which may enhance the value and utility of the proposed concepts.

Figure 2:
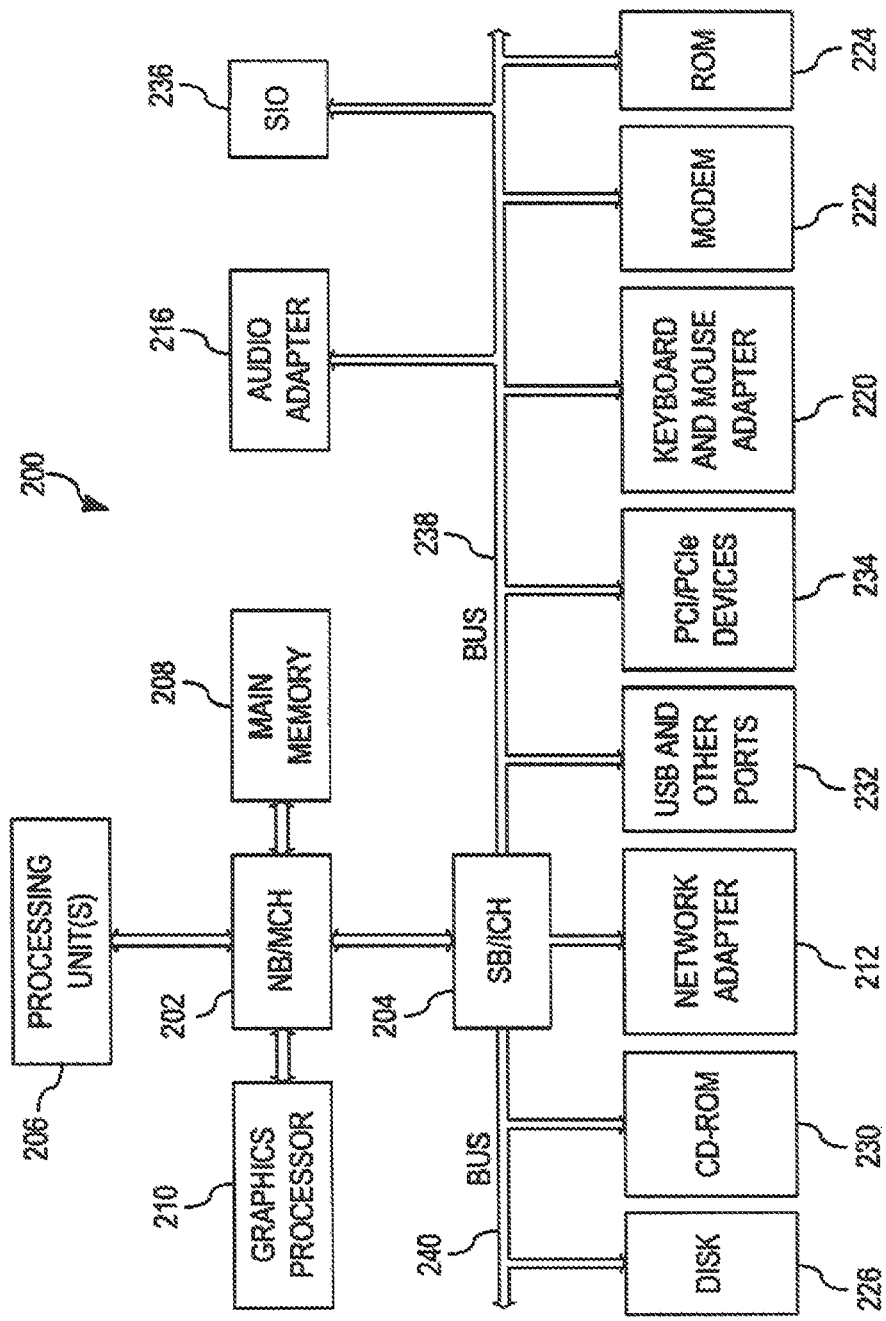
FIG. 2 is a block diagram of an example system in which aspects of the illustrative embodiments may be implemented.

Illustrative embodiments may be utilized in many different types of messaging processing environments. In order to provide a context for the description of elements and functionality of the illustrative embodiments, FIGS. 1 and 2 are provided hereafter as example environments in which aspects of the illustrative embodiments may be implemented. It should be appreciated that FIGS. 1 and 2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data storage system in which aspects of the illustrative embodiments may be implemented. Distributed system 100 may include a network of computers in which aspects of the illustrative embodiments may be implemented. The distributed system 100 contains at least one network 102, which is the medium used to provide communication links between various devices and computers connected together within the distributed data processing system 100. The network 102 may include connections, such as wire, wireless communication links, or fiber optic cables.

In the depicted example, first server 104 and second server 106 are connected to network 102 along with storage unit 108. In addition, clients 110, 112, and 114 are also connected to network 102. Clients 110, 112, and 114 may be, for example, personal computers, network computers, or the like. In the depicted example, first server 104 provides data, such as boot files, operating system images, and applications to clients 110, 112, and 114. Clients 110, 112, and 114 are clients to first server 104 in the depicted example. Distributed processing system 100 may include additional servers, clients, and other devices not shown.

In the depicted example, distributed system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, distributed system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

FIG. 2 is a block diagram of an example system 200 in which aspects of the illustrative embodiments may be implemented. System 200 is an example of a computer, such as client 110 in FIG. 1, in which computer usable code or instructions implementing the processes for illustrative embodiments of the present invention may be located.

In the depicted example, system 200 employs a hub architecture including a north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP) (not shown in FIG. 2).

In the depicted example, local area network (LAN) adapter 212 connects to SB/ICH 204. Audio adapter 216, keyboard and a mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through first bus 238 and second bus 240. PCI/PCIe devices 234 may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through second bus 240. HDD 226 and CD-ROM drive 230 may use, for example, an integrated drive electronics (IDE) or a serial advanced technology attachment (SATA) interface. Super I/O (SIO) device 236 may be connected to SB/ICH 204.

An operating system runs on processing unit 206. The operating system coordinates and provides control of various components within system 200 in FIG. 2. As a client, the operating system may be a commercially available operating system. An object-oriented programming system, such as the Java™ programming system, may run in conjunction with the operating system and provides calls to the operating system from Java™ programs or applications executing on system 200.

As a server, system 200 may be, for example, an IBM® eServer™ System p® computer system, running the Advanced Interactive Executive (AIX®) operating system or the LINUX® operating system. System 200 may be a symmetric multiprocessor (SMP) system including a plurality of processors in processing unit 206. Alternatively, a single processor system may be employed.

Instructions for the operating system, the programming system, and applications or programs are located on storage devices, such as HDD 226, and may be loaded into main memory 208 for execution by processing unit 206. Similarly, one or more message processing programs according to an embodiment may be adapted to be stored by the storage devices and/or main memory 208.

The processes for illustrative embodiments of the present invention may be performed by processing unit 206 using computer usable program code, which may be located in a memory such as, for example, main memory 208, ROM 224, or in one or more peripheral devices 226 and 230.

A bus system, such as first bus 238 or second bus 240 as shown in FIG. 2, may comprise one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache found in NB/MCH 202 in FIG. 2.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like (not shown in FIGS. 1 and 2), may be used in addition to or in place of the hardware depicted in FIGS. 1 and 2. Also, the processes of the illustrative embodiments may be applied to a multiprocessor data processing system, other than the system mentioned previously, without departing from the spirit and scope of the present invention.

Moreover, system 200 may take the form of any of a number of different data processing systems including client computing devices, server computing devices, a tablet computer, laptop computer, telephone or other communication device, a personal digital assistant (PDA), or the like. In some illustrative embodiments, system 200 may be a portable computing device that is configured with flash memory to provide non-volatile memory for storing operating system files and/or user-generated data, for example. Thus, system 200 may essentially be any known or later-developed data processing system without architectural limitation.

A proposed concept may enhance a data access control system by identifying the owner of a row on a physical storage level and then implementing row-based access by creating table-level restrictions. Embodiments may enable an associated owner of a database record to be identified (e.g. from owner identification information included in the database record) and the permissions of the identified owner may then be inherited by the database record. Such proposals can extend or improve the data access control capabilities or security of a relational database system.

In healthcare, and other regulated sectors, it may be important to know who 'owns' a particular piece of data. For example, in healthcare, a Blood Pressure reading is uniquely associated with (or owned by) one patient. This information is deemed to be regulated as 'Protected Health Information' (PHI) under US HIPAA regulations (other countries may have similar laws). Proposed embodiments may be premised on a concept of a 'Master Record' representing the real-world entity (for example, legal entity) to whom the data represented by the database record belongs. This Master Record may be stored as a row in a data table, and the permissions associated with this row may then be inherited by all records that designate that row or master record as being their associated 'owner'.

In the following section there are proposed extensions to the canonical DBMS physical storage model in support of OORBA.

There are various types of database physical storage, for example, ISAM, B+ tree and so on, and when a SQL query is committed to the database engine, the related records data are fetched from physical storage, then translated to database records. The records data not only contains attributes which are defined by a user, but also contains metadata which is used by a database engine.

Figure 3:
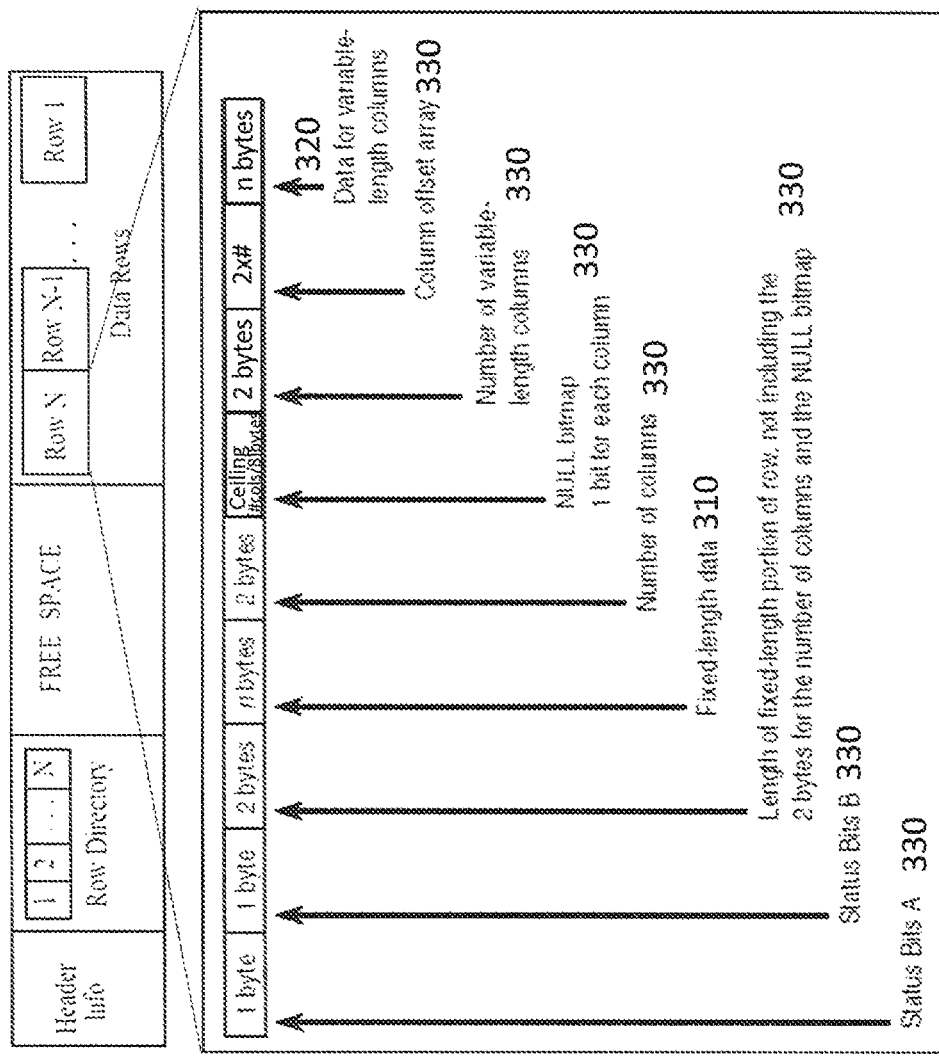
FIG. 3 is a simplified block diagram illustrates a record storage schema of a conventional relational database (RDBS)

FIG. 3 illustrates one embodiment of what a record storage looks like in a typical/conventional relational database (RDBS).

The data is stored in fixed-length data 310 and variable-length data 320 area, while all the rest are metadata 330 which facilitates the database engine in understanding what the structure of the data looks like and how to read each record attribute from the storage.

Figure 4:
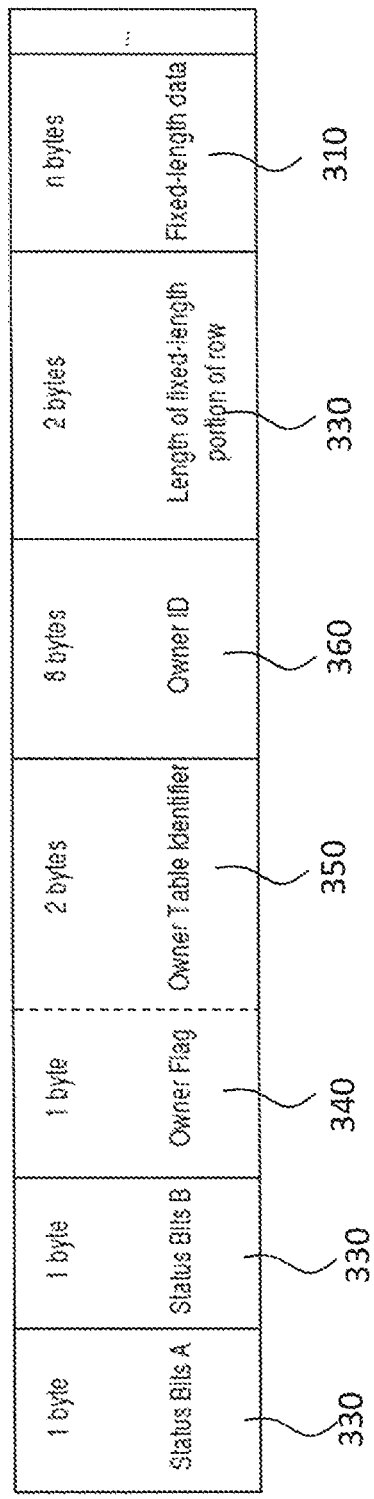
FIG. 4 illustrates additional metadata fields of a record storage schema according a proposed embodiment.

Proposed embodiments may extend the above-mentioned record storage schema by adding extra metadata fields. By way of example, FIG. 4 illustrates the additional metadata fields that are employed in a proposed embodiment. The additional meta-data fields in this exemplary embodiment are designated as follows: Owner Flag 340; Owner Table Identifier 350; and Owner ID 360. Here, it is noted that although the DB2 physical storage scheme is used in this example, the same principles apply to any other relational database.

Owner Flag 340 may be a one-byte field which used to indicate if the record has a dedicated owner. If there is a dedicated owner, the following ten bytes contains Owner Table Identifier 350 and Owner ID 360 fields. Otherwise, the Owner Table Identifier 350 and Owner ID 360 fields may not be present. The Owner Table Identifier 350 field may be used to store the ID of the table containing the Master Record(s) for data ownership. This ID may typically be an identifier from a database system table which is used to store the meta-data of user tables. Owner ID 360 field may be used to store the primary key of the Master Record, which may be a 64-bit integer for example. Again, the Owner Table Identifier 350 and Owner ID 360 fields may only appear if the Owner Flag 340 field is true/affirmative (e.g. if the value of the Owner Flag 340 field is set to 0x01).

When a database engine retrieves the record from physical storage, it may check if the 3rd byte (i.e. Owner Flag 340) is "1" or "0", and if it is "1", then the next 2 bytes is Owner Table Identifier 350 which may be used to tell which table the owner of the record is from, and the following 8 bytes is Owner ID 360 (i.e. the primary key) of the record's owner. Thus, with only one read operation, the database engine may establish whether a current user has access to the retrieved record. Conversely, if the 3rd byte is "0", the data engine may just follow its original logic to read the fixed and variable length attributes. Here, it is noted that the owner table's primary key may be an integer, for example a 64-bit integer.

According to some embodiments of the present invention, there may be provided an extension of DDL to ensure newly created rows have the correct data ownership information.

To write the correct Data Ownership information to a new database record, the DBMS may need to know how to locate the correct Master Record to associate with the new or updated database record. Proposed embodiments may achieve this by extending meta-data associated with an 'owned' table to include information about how to retrieve the ID of the Master Record associated with a row in the 'owned' data table. In this way, the master record information may be used when creating new records or updating existing records. For example, the database engine may insert or update the ownership information into the physical storage accordingly.

The meta-data for how to locate the master record ID may be added to the owned data table by extending the existing foreign key relationship meta-data. This additional meta-data may be declared using an extension to the Foreign Key DDL syntax.

In order to create a data ownership relationship between Data Table A (owner) and Data Table B (owned), there may exist a chain of foreign key relationships between Data Table B and Data Table A such that any row in B may trace ancestry back to a unique master record ('Owner') in Data Table A via a chain of Foreign Key constraints. As such, the concept of 'Ownership' may be attached to a Foreign Key Constraint.

By way of example, the following DDL syntax may be proposed:

First, declare foreign key relationship between A and B.

ALTER TABLE B ADD CONSTRAINT FK_B_A FOREIGN KEY ("SAMPLE_ID") REFERENCES "A" ("SAMPLE_ID");

and then declare Ownership between A and B.

ALTER FOREIGN KEY FK_B_A ADD OWNERSHIP TO A;

With ownership attached to the foreign key constraints, when creating a new record of entity B, the database engine may easily calculate which record of entity A owns it, and fill in its data to the ownership fields of physical storage.

In systems that store medical data, significant portions of the schema may be concerned with data relating to a single patient. In these cases, the records form a hierarchy with respect to the entity representing a patient. In proposed embodiments, these entities containing medical data about a patient may be connected to the patient entity via a chain of foreign keys annotated with ownership information.

Figure 5:
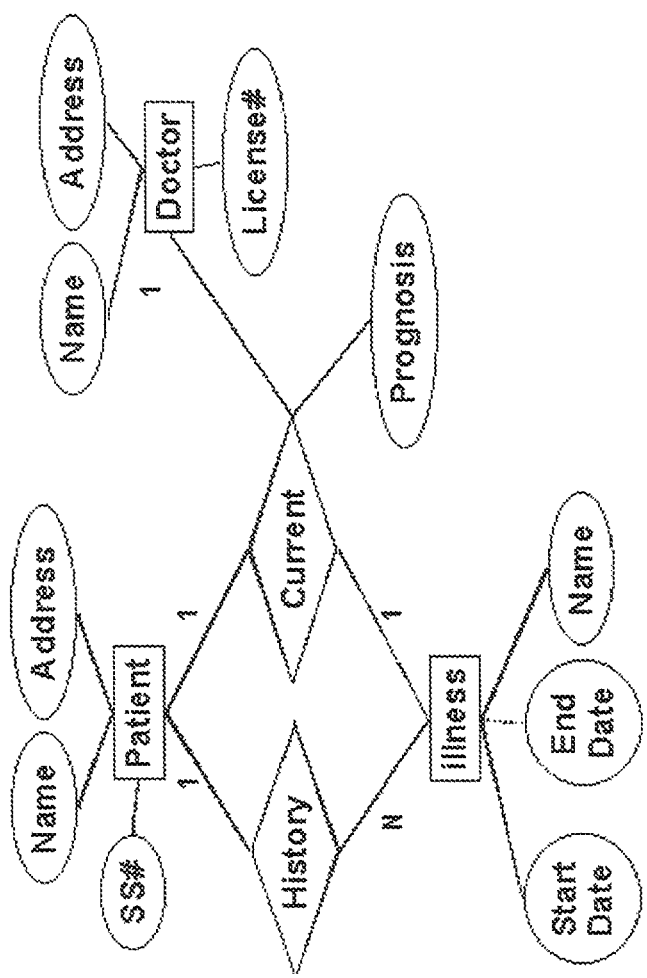
FIG. 5 is a diagram illustrating an exemplary hierarchical relationship between information.

For example, take the hierarchical diagram of FIG. 5. In the example if FIG. 5, the patient entity is the owner of both 'History' and 'Illness'. The owner relationship declaration may be expressed as:

ALTER TABLE HISTORY ADD CONSTRAINT FK_HIST_PAT FOREIGN KEY ("PATIENTID") REFERENCES "PATIENT"("PATIENTID");

ALTER FOREIGN KEY FK_HIST_PAT ADD OWNERSHIP TO PATIENT;

ALTER TABLE ILLNESS ADD CONSTRAINT FK_ILL_HIST FOREIGN KEY ("HISTORYID") REFERENCES "HISTORY"("HISTORYID");

ALTER FOREIGN KEY FK_ILL_HIST ADD OWNERSHIP TO PATIENT;

Once a chain or path of foreign keys has been established between a leaf entity (owned) and a root entity (owner), dropping of foreign keys in the middle of a chain of ownership may not be permitted. Ownership may be dismantled from leaf to root, for example:

ALTER TABLE HISTORY DROP CONSTRAINT FK_HIST_PATH;—Not permitted since there is an ownership chain associated with FK_HIST_PATH ALTER FOREIGN KEY FK_HIST_PAT DROP OWNERSHIP TO PATIENT;—Not permitted, as the OWNERSHIP to patient is part of a chain of ownership that includes illness ALTER FOREIGN KEY FK_ILL_HIST DROP OWNERSHIP TO PATIENT;—Permitted, as this is a leaf link in an ownership chain going back to PATIENT ALTER TABLE ILLNESS DROP CONSTRAINT FK_ILL_HIST;—Permitted as there is no more OWNERSHIP implied on this Foreign Key relationship.

Proposed embodiment may introduce the concept of a SYSTEM_OWNER Table

SYSTEM_OWNER table may be a system table which is introduced by embodiments to store the owner relationships. Once the owner relationship is declared, the database engine may add a new entry to SYSTEM_OWNER table.

By way of example, taking Illness and Patient from the example of FIG. 5, the table may look like:

| Child | Parent | FK_ConstraintID |
|---|---|---|
| Illness | Patient | FK_ILL_HIST |

When a new record is inserted, the database engine may search the SYSTEM_OWNER table to check if the entity is a child entry in the table, and if it is, database engine may find the map from child entry to the parent entry by searching through the foreign key constraints.

Owner Relationships Inheritance

The owner relationship is transitive, which means if record A owns record B, and record B is the owner of record C, then A is also the owner of C. The inheritance of owner relationships may make a tree structure in which all the descendants of the Master Record (root node of the tree) automatically inherit the same row-based authorization rule(s) that apply to the Master Record.

This may place constraints on schema design and cause ownership anomalies from schema changes. For example:

(i) due to the design of the physical record structure, it may be assumed that entities that are to be used as master records must have a primary key that is a 64-bit integer. Although the current scheme allows for 2^16 Master Record Entity Types. For example, Patient could be one owner type while Provider (Doctor) is another. The physical storage design only allows for a given database record to be owned by one Master Record.

(ii) Once a chain or path of foreign keys has been established between a leaf entity (owned) and a root entity (owner), dropping of foreign keys in the middle of a chain of ownership may not be permitted. Instead, it may be that ownership must be dismantled from leaf to root.

(iii) Dropping ownership from a foreign key may not result in the removal of ownership records from physical storage, such that the ownership data remains. This may lead to ownership anomalies. Database management systems that implement data ownership concepts proposed herein may therefore include maintenance utilities that may perform updates to ownership records for the purpose of maintaining consistency and removing ownership anomalies Calculating a User's Right to Access Data belonging to a Data Owner It will now be described how existing row-based security authorization models may be extended to work with the proposed owner relationship inheritance model. Here, an exemplary algorithm used to determine whether the current user id is authorized to access a given record will be described. The algorithm assumes that the administrator or schema owner has already defined a 'root' Owner entity.

a) A database user with administrator privileges applies row-based security to records on the root Owner table; and b) Any database records that are declared as being descendants of master records in the root owner table (via addition of ownership to foreign key relationships) will inherit any row-based permission grants from their ancestor record on the owner table.

When a select is performed on a table that is subject to data-ownership the following may occur:

I) For each record, the database engine checks whether the record includes owner identification data.

II) If owner identification data is included, the database engine checks to see whether data ownership is still valid for that entity via the SYSTEM_OWNER record. However, this step may be optimized or omitted at runtime based on database management policy.

III) If the record includes valid owner identification data, then the owner identification data is used to perform a lookup of the row-based authorization data associated with the master record. If the active user id has permission to access the master record, then they have permission to access the current record and so the record is added to the result set.

In an extension of the above exemplary embodiment, a fourth step may added:

IV) If the master record is itself an owned database record, then the process is repeated recursively.

The following simple example is used to illustrate how this works:

Create tables for patient, history and illness

CREATE TABLE PATIENT("PATIENTID" BIGINT not null, "NAME" CHARACTER(256) not null, "MEDICALRECORDNR" BIGINT);

ALTER TABLE PATIENT ADD CONSTRAINT PATIENT PRIMARY KEY("PATIENTID");

CREATE TABLE HISTORY("HISTORYID" BIGINT not null, "PATIENTID" BIGINT not null, "INITIATED" DATE not null);

ALTER TABLE HISTORY ADD CONSTRAINT HISTORY PRIMARY KEY("HISTORYID");

History is a child of Patient (i.e. a patient can 'own' many history items)

ALTER TABLE HISTORY ADD CONSTRAINT FK_HIST_PAT FOREIGN KEY ("PATIENTID") REFERENCES "PATIENT"("PATIENTID");

Add ownership to the Foreign Key
ALTER FOREIGN KEY FK_HIST_PATH ADD OWNERSHIP TO PATIENT;
CREATE TABLE ILLNESS("ILLNESSID" BIGINT not null, "HISTORYID" BIGINT not null, "SUMMARY" CHARACTER(256));
ALTER TABLE ILLNESS ADD CONSTRAINT ILLNESS PRIMARY KEY("ILLNESSID");
Illness is a child of history
ALTER TABLE ILLNESS ADD CONSTRAINT FK_ILL_HIST FOREIGN KEY ("HISTORYID") REFERENCES "HISTORY"("HISTORYID");
Add ownership to the Foreign Key
ALTER FOREIGN KEY FK_ILL_HIST ADD OWNERSHIP TO PATIENT;
Add some patients
INSERT INTO PATIENT ("PATIENTID", "NAME", "MEDICALRECORDNR") VALUES (1, 'Jane Worthington', 342445);
INSERT INTO PATIENT ("PATIENTID", "NAME", "MEDICALRECORDNR") VALUES (2, 'Josh Clancy', 342446);
INSERT INTO PATIENT ("PATIENTID", "NAME", "MEDICALRECORDNR") VALUES (3, 'Susan Harte', 342447);
INSERT INTO PATIENT ("PATIENTID", "NAME", "MEDICALRECORDNR") VALUES (4, 'Simon Bernstein', 342448);
Add some Illnesses for Jane and Josh
INSERT INTO HISTORY ("HISTORYID", "PATIENTID", "INITIATED") VALUES (1, 1, '2016-06-01');
INSERT INTO HISTORY ("HISTORYID", "PATIENTID", "INITIATED") VALUES (2, 1, '2016-06-03');
INSERT INTO HISTORY ("HISTORYID", "PATIENTID", "INITIATED") VALUES (3, 2, '2016-01-01');
INSERT INTO ILLNESS ("ILLNESSID", "HISTORYID", "SUMMARY") VALUES (1, 1, 'Jane W presenting with sore throat');
INSERT INTO ILLNESS ("ILLNESSID", "HISTORYID", "SUMMARY") VALUES (2, 1, 'Jane complains of backache');
INSERT INTO ILLNESS ("ILLNESSID", "HISTORYID", "SUMMARY") VALUES (3, 2, 'Jane—pain spread to shoulders, upper back');
INSERT INTO ILLNESS ("ILLNESSID", "HISTORYID", "SUMMARY") VALUES (4, 3, 'Josh—infected toenail');
Add permission for Red CareTeam to access Jane's record and by implication all data belonging to Jane
CREATE PERMISSION RedTeamP ON PATIENT AND OWNED DATA FOR ROWS WHERE "PATIENTID"=1 AND VERIFY_ROLE_FOR_USER(USER, 'RedTeamMemberRole') ENFORCED FOR ALL ACCESS ENABLE;
CREATE PERMISSION BlueTeaP ON PATIENT AND OWNED DATA FOR ROWS WHERE "PATIENTID"=2 AND VERIFY_ROLE_FOR_USER(USER, 'BlueTeamMemberRole') ENFORCED FOR ALL ACCESS ENABLE;

In this example with user 'harriet' who has the role 'RedTeamMemberRole' but not the role 'BlueTeamMemberRole. the user 'harriet' may execute the following query:
SELECT*FROM ILLNESS;
In response, the database engine may check the SYSTEM_OWNER table to see whether ownership-based security is enabled for the ILLNESS table. Upon finding it is, the following result set may be checked to determine which rows can be included:

(i) The database engine checks result where "ILLNESSID"=1. This ownership data points to the Patient table where "PATIENTID"=1. This record as a row permission that requires the user to have the role 'RedTeamMemberRole'. Since user 'harriet' has this role, permission is granted and this record is added to the result set.

(ii) The database engine checks result where "ILLNESSID"=2. This ownership data points to the Patient table where "PATIENTID"=1. This record as a row permission that requires the user to have the role 'RedTeamMemberRole'. Since user 'harriet' has this role, permission is granted and this record is added to the result set.

(iii) The database engine checks result where "ILLNESSID"=3. This ownership data points to the Patient table where "PATIENTID"=1. This record as a row permission that requires the user to have the role 'RedTeamMemberRole'. Since user 'harriet' has this role, permission is granted and this record is added to the result set.

(iv) The database engine checks result where "ILLNESSID"=4. This ownership data points to the Patient table where "PATIENTID"=2. This record as a row permission that requires the user to have the role 'BlueTeamMemberRole'. Since user 'harriet' does not have this role, this record is not added to the result set.

From the description provided above, it will be understood that some embodiments may identify (using ownership data fields comprising identification information) the owner of a row on physical storage level, and then achieve row-based access by creating table-level restrictions. By way of example, such embodiments may extend a conventional record storage schema by adding one or more extra metadata fields for identifying a master record (e.g. owner).

Extension of DDL may therefore be proposed through the addition of extra metadata detailing ownership of data, and this may be done at the physical storage level.

A strong linkage between protected information and the records that identify the owner of the protected information may therefore be provided by proposed embodiments. This may allow for highly efficient authorization of access to the records, since de-identification/re-identification processes may be avoided. Embodiments may therefore avoid reliance on a de-identification/re-identification process in order to obscure or protect information.

In some embodiments, there may be provided a system comprising a processing arrangement adapted to carry out any method previously described with reference to FIGS. 1 to 6.

Figure 6:
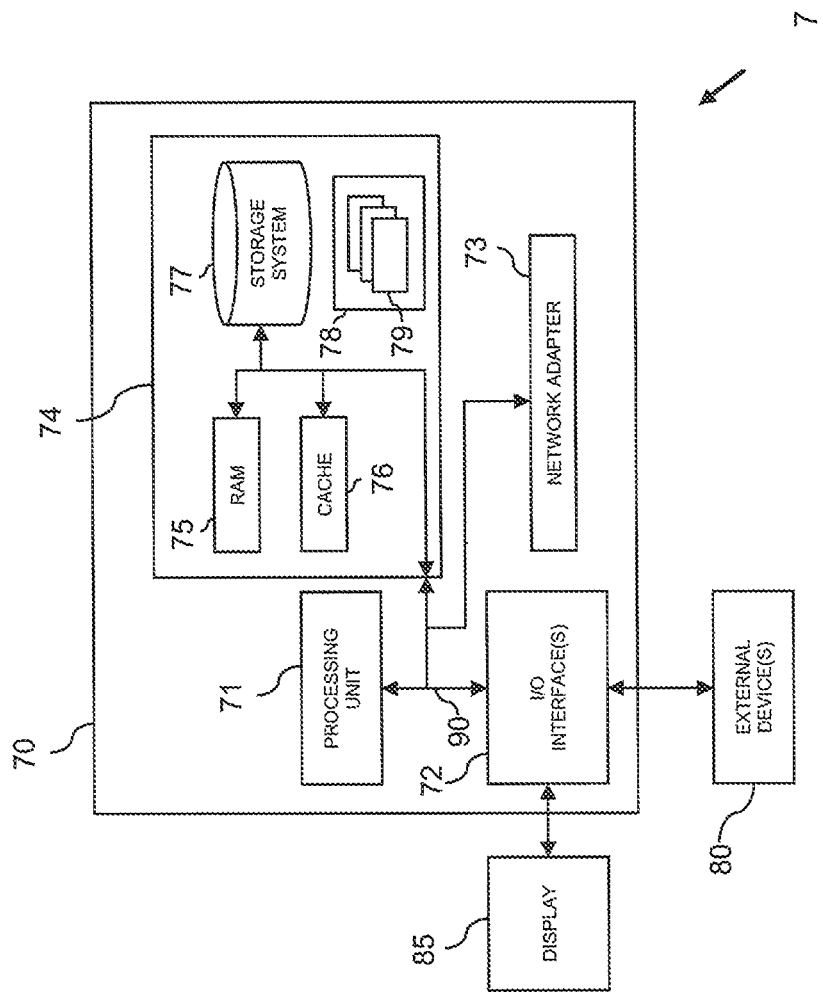
FIG. 6 illustrates a system for controlling access to protected information stored in a database according to an embodiment.

By way of example, as illustrated in FIG. 6, embodiments may comprise computer system/server 70, which may form part of networked system 7. The components of computer system/server 70 may include, but are not limited to, one or more processing arrangements, for example comprising processors or processing units 71, system memory 74, and bus 90 that couples various system components including system memory 74 to processing unit 71.

Bus 90 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 70 typically includes a variety of computer system readable media. Such media may be any available media that is accessible by computer system/server 70, and it includes both volatile and non-volatile media, removable and non-removable media.

System memory 74 can include computer system readable media in the form of volatile memory, such as random access memory (RAM) 75 and/or cache memory 76. Computer system/server 70 may further include other removable/non-removable, volatile/non-volatile computer system storage media. By way of example only, system memory 74 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 90 by one or more data media interfaces. As will be further depicted and described below, system memory 74 may include at least one program product having a set (e.g., at least one) of program modules that are configured to carry out the functions of embodiments of the invention.

Program/utility 78, having a set (at least one) of program modules 79, may be stored in system memory 74 by way of example, and not limitation, as well as an operating system, one or more application programs, other program modules, and program data. Each of the operating system, one or more application programs, other program modules, and program data or some combination thereof, may include an implementation of a networking environment. Program modules 79 generally carry out the functions and/or methodologies of embodiments of the invention as described herein.

Computer system/server 70 may also communicate with one or more external devices 80 such as a keyboard, a pointing device, display 85, etc.; one or more devices that enable a user to interact with computer system/server 70; and/or any devices (e.g., network card, modem, etc.) that enable computer system/server 70 to communicate with one or more other computing devices. Such communication can occur via Input/Output (I/O) interfaces 72. Still yet, computer system/server 70 can communicate with one or more networks such as a local area network (LAN), a general wide area network (WAN), and/or a public network (e.g., the Internet) via network adapter 73. As depicted, network adapter 73 communicates with the other components of computer system/server 70 via bus 90. It should be understood that although not shown, other hardware and/or software components could be used in conjunction with computer system/server 70. Examples, include, but are not limited to: microcode, device drivers, redundant processing units, external disk drive arrays, RAID systems, tape drives, and data archival storage systems, etc.

In the context of the present application, where embodiments of the present invention constitute a method, it should be understood that such a method is a process for execution by a computer, i.e. is a computer-implementable method. The various steps of the method therefore reflect various parts of a computer program, e.g. various parts of one or more algorithms The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a storage class memory (SCM), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method (CIM) for controlling access to protected information stored in a database, the CIM comprising:
    identifying a set of database records in various data tables as master records, with each master record having an associated set of authorization rule(s);
    storing, in each database record of the database, one or more ownership data fields including owner identification information for identifying a master record associated with the database record;
    retrieving a retrieved database record of the database;
    analyzing the owner identification information of the one or more ownership data fields of the retrieved database record to identify the master record associated with the retrieved database record;
    controlling access to the retrieved database record using the set of authorization rule(s) of the master record associated with the retrieved database record;
    associating a newly created or updated database record in the data with the master record, with the association including processing the newly created or updated database record by analyzing an ownership meta-data table to determine which master record the database record should be associated with; and
    creating an ownership inheritance structure to graphically represent the data ownership rules, with the ownership inheritance structure being a tree structure that includes one root node and at least one leaf node;
    wherein the identification of the master records in the data table further includes:
        extending the Data Definition Language (DDL) to allow a database designer to define data ownership rules,
        extending the DDL language processor to allow the set of authorization rule(s) to be stored in the ownership meta-data table for the database, and
        extending the Database Management System to process the ownership meta-data table so as to identify the master records in the database;
    wherein the one or more ownership data fields includes: metadata, a flag field comprising information for indicating whether the database record has an associated master record, an owner identification field comprising information identifying the master record associated with the database record, a key of the master record associated with the database record, with the key being an integer, a table identification field comprising information identifying the data table comprising the master record associated with the database record, and/or a record identification field which identifies the master record associated with the database record;
    wherein the Database Management System further includes:
        extensions to the Data Definition Language that allow the database designer to declare information indicative of ownership relationships between tables containing master data and other tables containing data related to that master data, with the ownership relationships information being stored in an ownership meta-data table, and
        extensions in the Database Management System that are adapted to be triggered when a new database record is created or an existing record is updated so as to process the one or more ownership data fields to determine which master records, if any, that database record should be associated with;

wherein the database includes the set of database records in various data tables as master records;

wherein the database is a relational database;

the protected information includes protected health information; and the owner relationship of the one or more ownership data fields of the retrieved database record(s) is a hierarchical relationship.

2. The CIM of claim 1 wherein the owner relationship of the one or more ownership data fields of the retrieved database record(s) is transitive.

3. The CIM of claim 1 wherein:

the root node of the tree structure represents the master record and the at least one leaf node represents an updated database record; and the at least one leaf node automatically inherits the row-based authorization rule(s) that are applied to the master record.

* * * * *